United States Patent [19]

Lo et al.

[11] 4,309,552
[45] Jan. 5, 1982

[54] SYNTHESIS OF 4-NITRO-1,2-HYDROCARBYL PYRAZOLIDINES AND PROCESS FOR PREPARATION THEREOF

[75] Inventors: Young S. Lo; Harry R. Munson, Jr., both of Richmond, Va.

[73] Assignee: A. H. Robins Company, Inc., Richmond, Va.

[21] Appl. No.: 176,175

[22] Filed: Aug. 7, 1980

[51] Int. Cl.³ ........................................... C07D 231/04
[52] U.S. Cl. .................................................... 548/356
[58] Field of Search ........................................ 548/356

[56] References Cited

U.S. PATENT DOCUMENTS 4,207,327  6/1980  Lunsford et al. ............... 424/273 P

OTHER PUBLICATIONS

Lüttringhaus et al., Chem. Abst. 1958, vol. 52, p. 9080b.
Snider et al., J. Org. Chem. 1979, vol. 44, No. 2, pp. 218-21.

*Primary Examiner*—John M. Ford
*Assistant Examiner*—Natalia Harkaway

[57] ABSTRACT

4-Nitro-1,2-hydrocarbyl pyrazolidines are prepared by a novel route from 1,2-disubstituted hydrazines and 1,3-di-(secondary amino)-2-nitropropanes and reduced to the corresponding 4-amino-1,2-hydrocarbyl pyrazolidines, which latter compounds are intermediates in the preparation of certain pharmaceutical benzamides.

The novel 4-nitro-1,2-hydrocarbyl pyrazolidines have the formula:

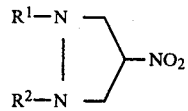

wherein $R^1$ and $R^2$ are selected from loweralkyl, lowercycloalkyl or phenyl-loweralkyl and may be the same or different.

7 Claims, No Drawings

SYNTHESIS OF 4-NITRO-1,2-HYDROCARBYL PYRAZOLIDINES AND PROCESS FOR PREPARATION THEREOF

BACKGROUND OF THE INVENTION

1. Field of the Invention

This invention is concerned with a novel process for preparing 4-amino-1,2-hydrocarbyl-pyrazolidines via novel 4-nitro-1,2-hydrocarbyl pyrazolidines, all intermediates to the preparation of N-(1,2-hydrocarbyl-4-pyrazolidinyl benzamides, which latter compounds have utility in controlling emesis and gastric emptying in warm-blooded animals.

2. Description of the Prior Art

The 4-nitro-1,2-hydrocarbyl-pyrazolidines of this invention have not previously been disclosed and the method of preparation from 1,2-disubstituted hydrazines with 1,3-bis-(disubstituted amino)-2-nitropropanes is believed to be novel. The 4-amino-1,2-hydrocarbyl-pyrazolidines have not previously been prepared by the method of this invention, but are known compounds used in the preparation of the benzamides as described in U.S. application Ser. No. 41,461 (U.S. Pat. No. 4,206,327). In that disclosure, 4-amino-1,2-hydrocarbyl pyrazolidines are prepared from 4-halo-1,2-hydrocarbyl-pyrazolidines and ammonia.

SUMMARY OF THE INVENTION AND OBJECTS

The process of this invention involves a novel reaction of 1,2-disubstituted hydrazine acid salts with 1,3-bis-(disubstituted amino)-2-nitropropanes to give novel 4-nitro-1,2-hydrocarbyl-pyrazolidines which are reduced to 4-amino-1,2-hydrocarbyl-pyrazolidines. The process does not require isolation of the 4-nitro-1,2-hydrocarbyl-pyrazolidines from the initial solution before reduction can be carried out.

The novel precursors, the 4-nitro-1,2-hydrocarbyl-pyrazolidines, of this invention have the formula:

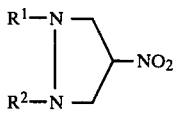
II wherein $R^1$ and $R^2$ are selected from loweralkyl, lowercycloalkyl or phenyl-loweralkyl and may be the same or different and the hydrocarbyl moieties are further defined in the definitions hereinbelow.

The 4-amino-1,2-hydrocarbyl-pyrazolidines having the formula:

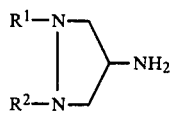
I are produced as a final product of this invention and have utility in the preparation of hereinabove-described benzamides wherein $R^1$ and $R^2$ are as defined above and below.

It is therefore an object of the present invention to provide novel 4-nitro-1,2-hydrocarbyl-pyrazolidine intermediates leading to 4-amino-1,2-hydrocarbyl pyrazolidine intermediates for the preparation of N-(4-pyrazolidinyl) benzamides which have utility in controlling gastric disorders.

Another object is to provide novel methods of preparing both the 4-nitro and 4-amino-1,2-hydrocarbyl pyrazolidines.

Additional objects will be apparent to one skilled in the art and still other objects will become apparent hereinafter from the following description of the best mode of carrying out the present invention and from the appended claims.

DETAILED DESCRIPTION OF THE INVENTION

The present invention encompasses a method of producing 4-amino-1,2-hydrocarbylpyrazolidines of Formula I as set forth in the description of the process herein, in the equations and definitions following. The invention also encompasses the method of producing the precursor 4-nitro-1,2-hydrocarbyl-pyrazolidines of Formula II and as composition of matter of the latter.

In the first step of the process a disubstituted hydrazine acid salt (IV) is reacted with a 1,3-bis (disubstituted amino)-2-nitropropane (III) to give the 4-nitro-1,2-hydrocarbyl-pyrazolidines (II) generally represented by the following equation:

$R^1NHNHR^2 \cdot 2HX + R^3R^4N-CH_2CHNO_2CH_2NR^5R^6 \longrightarrow$

IV  III

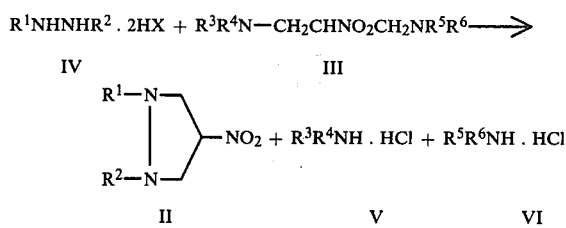

II  V  VI wherein $R^1$ and $R^2$ are selected from loweralkyl, lowercycloalkyl or phenyl-loweralkyl and may be the same or different, and $R^3$, $R^4$, $R^5$ and $R^6$ are selected from loweralkyl and may be the same or different and $R^3$ and $R^4$ or $R^5$ and $R^6$ taken together with the adjacent nitrogen atom may form a heterocyclic residue.

In the second step of the process the foregoing 4-nitro-1,2-hydrocarbyl-pyrazolidines (II) are reduced to give the corresponding 4-amino-1,2-hydrocarbyl-pyrazolidines (I) as represented by the following equation:

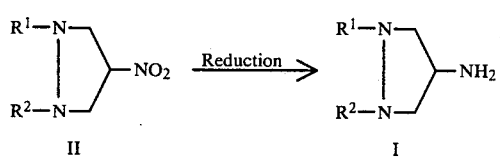

II  I wherein $R^1$ and $R^2$ are as defined hereinabove. Any number of reduction agents will serve to convert the nitro compounds to the amino derivatives such as catalytic hydrogenation with hydrogen using metal catalysts, iron powder in acetic acid solvent, zinc dust in basic aqueous alcohol solution, tin-hydrochloric acid, hydrides such as lithium aluminum hydride and diborane, sodium thiosulfate or ammonium sulfide. See Beuler, C. A. & Pearson, D. E. "Survey of Organic Synthesis" I and II (1970 and 1977) Chapter 8 each volume, Wiley Interscience Publ., N. Y., N. Y.

In further definition of symbols, the term "loweralkyl" includes straight and branched chain radicals containing 1 to 8 carbon atoms as, for example, methyl, ethyl, propyl, isopropyl, n-butyl, tertiary butyl, amyl, isoamyl, n-hexyl, n-heptyl, and n-octyl radicals. A "lower-alkoxy" radical has the formula -O-loweralkyl.

The term "lower cycloalkyl" as used herein includes primarily cyclic alkyl radicals containing from three up to twelve carbon atoms inclusive and includes such groups as cyclobutyl, cyclopentyl, cyclohexyl, cycloheptyl, methylcyclopentyl, ethyl-cyclohexyl and the like.

The term "phenyl-loweralkyl" as used herein includes the unsubstituted phenyl-loweralkyl radical and phenyl-loweralkyl radicals wherein phenyl is substituted by any radical or radicals which are not reactive or otherwise interfering under the conditions of reaction described herein such as loweralkyl, lower-alkoxy, trifluoromethyl, halo, acetamido, sulfamoyl, and the like. The substituted phenyl-loweralkyl radicals have preferably no more than three substituents on phenyl such as those given above and, furthermore, these substitutents can be in various available positions of the phenyl nucleus and when more than one substituent is present, can be the same or different and can be in various position combinations relative to each other. The loweralkyl and lower-alkoxy substituents each have preferably from one to four carbon atoms which can be arranged as straight or branched chains. Examples of the preferred substituents on phenyl of phenyl-lower alkyl are methyl, ethyl, propyl, butyl, fluoro, bromo, chloro, methoxy, ethoxy, propoxy, and butoxy radicals.

Included in the term "phenyl-loweralkyl" are such groups as benzyl, phenethyl, phenpropyl, α-methylbenzyl, and the like.

By heterocyclic residue is meant such radicals as pyrrolidino, morpholino, piperidino, piperazino and the like.

The starting 1,2-disubstituted hydrazines (IV) of Step 1 are prepared by known methods. Symmetrical 1 and 2 disubstituted loweralkyl hydrazines are prepared by methods given in "Organic Synthesis" II, p. 208–211, unsymmetrical 1 and 2-disubstituted-loweralkyl and cycloalkyl hydrazines are prepared by methods given in "Chemistry of Open Chain Organic Nitrogen Compounds" by Smith, P.A.S., Vol. 2, Chapter 2, publ. W. A. Benjamin, Inc., N. Y. (1966). Symmetrical phenyl-loweralkyl and substituted-phenyl-loweralkyl hydrazines are prepared by reacting corresponding phenyl and substituted phenyl-loweralkyl azines with diborane. Unsymmetrical 1-phenyl-loweralkyl-2-loweralkyl or 1-phenyl-loweralkyl-2-cycloalkyl hydrazines are prepared by the method of U.S. Pat. No. 3,660,426. Symmetrical 1,2-cycloalkyl-hydrazines are prepared by the method of Cope, A. C. and Engelhart, J. E. in J. Amer. Chem. Soc. 90, 7092–7096.

The starting 1,3-bis-(disubstituted amino)-2-nitropropanes of Formula III are prepared by the method of Zief, M. and Mason, J. P. in J. Org. Chem. 8, 1–5 (1943) wherein, for example, morpholine and formaldehyde are reacted followed by reaction with nitromethane.

In step 1, and acid salt of 1,2-disubstituted hydrazine (IV) and the 1,3-bis-(disubstituted amino)-2-nitropropanes (III) are reacted in any non-interfering solvent or solvent mixtures at temperatures between room temperature and 150° C. preferably 60°–80° C. Suitable solvents are methanol, ethanol, 2-methoxy ethanol, isopropanol and the like, and mixtures of such alcohols with aromatic solvents such as toluene, benzene and the like. Halogenated solvents in mixtures with alcohols may also be used. Any suitable acid salts of the hydrazines may be used such as hydrochloride, hydrogen sulfate, etc. The amine hydrochlorides, V and VI, are separated by filtration.

In the reaction of step 1 as will be readily realized by one skilled in the art, the $-NR^3R^4$ and $-NR^5R^6$ radicals in the 1,3-positions on the nitro propane are transient and serve as proton acceptors and do not appear in the pyrazolidine structure. Thus, any member of $-NR^3R^4$ or $-NR^5R^6$ combinations on nitropropane within the scope of the definitions can be reacted with a given 1,2-disubstitituted hydrazine acid salt to produce the same 4-nitro-1,2-hydrocarbyl-pyrazolidine. However, the preferred structures are the heterocyclic residues formed by $R^3$ and $R^4$ and $R^5$ and $R^6$ with the adjacent nitrogen atom such as morpholine, pyrrolidine, and piperidine, inasmuch as fewer side reactions occur. Of these heterocyclic residues, the use of the 1,3-dimorpholine combination is a preferred embodiment of the invention. Thus, the preferred nitropropane starting reagent is 1,3-dimorpholino-2-nitropropane. A preferred 1,2-disubstituted hydrazine is 1,2-diethylhydrazine and a preferred acid salt thereof is the dihydrochloride.

As mentioned above, it is not essential to totally isolate the 4-nitro-1,2-hydrocarbyl-pyrazolidines from the solution in step 1 before proceeding to the next step, it being only necessary to filter off the amine salts V and VI. However, in that aspect of the invention involving the preparation of these 4-nitro-1,2-hydrocarbyl-pyrazolidines as individual entities in substantially pure form, the solvent of the reaction mixture is evaporated, the residue dissolved in non-polar solvent such as toluene and the resulting amine hydrochlorides V and VI are filtered off. The non-polar solvent is then evaporated to give the 4-nitro-1,2-hydrocarbyl-pyrazolidines (II). The compound may then be further purified by column chromatography. When the preferred 1,3-dimorpholino-2-nitropropane is used, V and VI will, of course, be identical, i.e., morpholino hydrochloride.

EXAMPLE 1

4-Nitro-1,2-diethyl-pyrazolidine

A stirred solution of 4.03 g. (0.025 moles) of 1,2-diethyl hydrazine dihydrochloride and 6.72 g. (0.026 moles) of 1,3-dimorpholino-2-nitropropane in a mixture of 28 ml of methanol and 16 ml of toluene was heated at reflux for 3 hours. The solvents were evaporated under reduced pressure and the residue was re-suspended in toluene. The solid (mostly morpholine hydrochloride) was removed by filtration, leaving a solution of the title compound in toluene. Evaporation of the toluene gave an oil weighing 5.1 g., the free base of the title compound with minor impurity. Column chromatography on Florisil, eluting with toluene, gave pure title compound which was obtained as an oil by evaporation of toluene under reduced pressure. The product was characterized as follows: Infra Red (CHCl$_3$, microns) 6.46 (S), 6.94 (M), 7.27 (S) and 9.82 (M); Nuclear Magnetic Resonance (CDCL$_3$,δ)=5.18 (m, 1H), 3.16-3.75 with weight center at 3.47 (m, 4H), 2.56 (q, 7.7H$_z$, 4H), 1.07 (t, 7.7 H$_z$, 6H); Mass Spec: M+ 173.

EXAMPLE 2

4-Nitro-1,2-diisopropyl-pyrazolidine

Following the procedure of Example 1, but substituting an equal molar amount of 1,2-diisopropyl hydrazine dihydrochloride for 1,2-diethyl hydrazine dihydrochloride, the title compound is obtained.

EXAMPLE 3

4-Nitro-1,2-diethyl-pyrazolidine

To a suspension of 3 g. (0.022 moles) potassium carbonate in 20 ml ethanol in an ice bath was added 1.8 g. (0.011 moles) diethyl hydrazine dihydrochloride monohydrate with stirring for about 5 min. To this was added 1.92 (0.011 moles) of 1,3-bis-dimethylamino-2-nitropropane and stirring continued at room temperature for 2.5 hr. The alcoholic solution was decanted from the solid and evaporated to give a dark oil. Diethyl ether was added to give a suspension. Magnesium sulfate was added and the liquid portion separated and evaporated to an oil. Nuclear Magnetic Resonance confirmed presence of the product with some contamination of starting nitro compound.

EXAMPLE 4

4-Nitro-1,2-Bis(4-methoxybenzyl)pyrazolidine

Di-(4-methoxybenzyl) azine was first prepared by reacting 2 moles of p-methoxybenzaldehyde with 1 mole hydrazine in isopropyl alcohol at 10° C. Di-(4-methoxybenzyl) hydrazine was obtained by reacting the azine with diborane in tetrahydrofurane under nitrogen atmosphere at or below 10° C. and isolated as an oil. The dihydrochloride salt of bis-(4-methoxybenzyl) hydrazine was obtained as white solid by mixing with hydrogen chloride gas in isopropanol followed by addition of methylene chloride and toluene (81% yield based on azine). 1,2-Di-(4-methoxybenzyl)hydrazine (3.5 g., 0.01 mole) and 1,3-dimorpholine-1,2-nitropropane (2.6 g., 0.01 mole) were suspended in a mixture of 30 ml of methanol and 20 ml of toluene and heated to reflux for 3 hr. The reaction mixture was evaporated to dryness and the residue extracted with toluene and filtered. The toluene filtrate was evaporated to give 3.5 g. brown oil which was purified by column chromatography using 10% diethyl ether - 90% methylene chloride on silica gel. Nuclear Magnetic Resonance and mass spectra confirmed the structure of title compound. The oil solidified after one day standing at room temperature.

EXAMPLE 5

Following the procedure of Example 1, but substituting an equal molar amount of the following for 1,2-diethyl hydrazine hydrochloride:
1,2-dicyclohexyl hydrazine dihydrochloride,
1-cyclohexyl-2-methyl hydrazine dihydrochloride,
1-isopropyl-2-methyl hydrazine dihydrochloride,
1-ethyl-2-methyl hydrazine dihydrochloride,
1-isopropyl-2-ethyl hydrazine dihydrochloride,
1-benzyl-2-methyl hydrazine dihydrochloride,
1-benzyl-2-ethyl hydrazine dihydrochloride,
1-cyclohexyl-2-ethyl hydrazine dihydrochloride,
1,2-dibenzyl hydrazine dihydrochloride,
1-(4-methoxybenzyl)-2-ethyl hydrazine dihydrochloride,
there are obtained:
4-nitro-1,2-dicyclohexyl-pyrazolidine,
4-nitro-1-cyclohexyl-2-methyl-pyrazolidine,
4-nitro-1-isopropyl-2-methyl-pyrazolidine,
4-nitro-1-ethyl-2-methyl-pyrazolidine,
4nitro-1-isopropyl-2-ethyl-pyrazolidine,
4-nitro-1-benzyl-2-methyl-pyrazolidine,
4-nitro-1-benzyl-2-ethyl-pyrazolidine,
4-nitro-1-cyclohexyl-2-ethyl-pyrazolidine,
4-nitro-1,2-dibenzyl-pyrazolidine,
4-nitro-1-(4-methoxybenzyl)-2-ethyl-pyrazolidine.

EXAMPLE 6

4-Amino-1,2-diethyl-pyrazolidine

To a solution of approximately 3.0 g (0.016 mole) of 4-nitro-1,2-diethyl-pyrazolidine in 100 ml of toluene was added 60 ml of anhydrous ethanol and 2 g Raney nickel (washed three times with anhydrous ethanol). The mixture was added and hydrogenated for three hours at about 30 psi. The mixture was filtered to give a light yellow solution. The solvents were evaporated at reduced pressure giving the colorless liquid, 1.95 g of the title product, b.p. 113°-115° C./40 mm. The dimaleate salt melted at 119°-120° C.

EXAMPLE 7

4-Amino-1,2-diethyl-pyrazolidine,

A stirred solution of 4.03 g (0.025 moles) of 1,2-diethylhydrazine dihydrochloride and 6.72 g. (0.026 moles) of 1,3-dimorpholino-2-nitropropane in a mixture of 28 ml of methanol and 16 ml of toluene was heated at reflux for 3 hours. The solvents were evaporated under reduced pressure and the residue was resuspended in 100 ml of toluene. The solid morpholine hydrochloride was removed by filtration, leaving a solution of 4-nitro-1,2-diethyl-pyrazolidine in solution. To the toluene solution was added 60 ml anhydrous ethanol and 2 g. of Raney Nickel which had been washed three times with anhydrous ethanol. The mixture was hydrogenated at about 30 psi. hydrogen pressure. The mixture was filtered carefully under nitrogen to prevent ignition. Evaporation of solvents and distillation at reduced pressure gave colorless liquid product weighing 1.95 g. (54% yield calculated on diethylhydrazine), b.p. 113°-115° C./40 mm.

EXAMPLE 8

Following the procedure of Example 6 but substituting an equal molar amount of the following for 4-nitro-1,2-diethyl-pyrazolidine:
4-nitro-1,2-dicyclohexyl-pyrazolidine,
4-nitro-1-cyclohexyl-2-methyl-pyrazolidine,
4-nitro-1-isopropyl-2-methyl-pyrazolidine,
4-nitro-1-ethyl-2-methyl-pyrazolidine,
4-nitro-1-isopropyl-2-ethyl-pyrazolidine,
4-nitro-1-benzyl-2-methyl-pyrazolidine,
4-nitro-1-benzyl-2-ethyl-pyrazolidine,
4-nitro-1-cyclohexyl-2-ethyl-pyrazolidine,
4-nitro-1,2-dibenzyl-pyrazolidine,
4-nitro-1,2-di(4-methoxybenzyl)pyrazolidine,
4-nitro-1-(4-methoxybenzyl)-2-ethyl-pyrazolidine,
there are obtained:
4-amino-1,2-dicyclohexyl-pyrazolidine,
4-amino-1-cyclohexyl-2-methyl-pyrazolidine,
4-amino-1-isopropyl-2-methyl-pyrazolidine,
4-amino-1-ethyl-2-methyl-pyrazolidine,
4-amino-1-isopropyl-2-ethyl-pyrazolidine,
4-amino-1-benzyl-2-methyl-pyrazolidine, 4-amino-1-benzyl-2-ethyl-pyrazolidine,
4-amino-1-cyclohexyl-2-ethyl-pyrazolidine,
4-amino-1,2-dibenzyl-pyrazolidine,
4-amino-1,2-di(4-methoxybenzylpyrazolidine,
4-amino-1-(4-methoxybenzyl)-2-ethyl-pyrazolidine.

EXAMPLE 9

Following the procedure of Example 7 but substituting an equal molar amount of the following for 1,2-diethyl-hydrazinedihydrochloride:
1-(4-chlorobenzyl)2-ethyl hydrazine dihydrochloride,
1,2-di(4-chlorobenzyl)hydrazine dihydrochloride,
1,2-di(4-trifluoromethylbenzyl)hydrazine dihydrochloride,
1,2-di(4-acetamidobenzyl)hydrazine hydrogen sulfate,
1,2-di(4-sulfamoylbenzyl)hydrazine dihydrochloride,
1,2-di(4-butoxybenzyl)hydrazine phosphoric acid salt,
there are obtained:
4-amino-1-(4-chlorobenzyl)-2-ethyl pyrazolidine,
4-amino-1,2-di(4-chlorobenzyl)pyrazolidine,
4-amino-1,2-di(4-trifluoromethylbenzyl)pyrazolidine,
4-amino-1,2-di(4-acetamidobenzyl)pyrazolidine,
4-amino-1,2-di(4-sulfamoylbenzyl)pyrazolidine,
4-amino-1,2-di(butoxybenzyl)pyrazolidine.

EXAMPLE 10

4-Amino-1,2-diisopropyl-pyrazolidine

Following the procedure of Example 6, but substituting an equal molar amount of 4-nitro-1,2-diisopropyl-pyrazolidine for 4-nitro-1,2-diethyl-pyrazolidine, the title compound is obtained.

EXAMPLE 11

4-Amino-1,2-diisopropyl-pyrazolidine Fumarate [1:2], Hemihydrate.

The free base obtained in Example 9 is reacted with fumaric acid to obtain the title compound, m.p. 157°–161° C.

EXAMPLE 12

Following the procedure of Example 4, but substituting equal molar amounts of the following for di(p-methoxybenzyl) hydrazine:
di-(3,4,5-trimethoxybenzyl)hydrazine,
bis-(2,4-dimethoxybenzyl)hydrazine,
bis-(2,4-dimethylbenzyl)hydrazine,
di-(α-methylbenzyl)hydrazine,
bis-(2,4-dimethoxyphenylethyl)hydrazine,
there are obtained:
4-nitro-1,2-di[(3',4',5'-trimethoxy)benzyl]pyrazolidine,
4-nitro-1,2-bis[(2',4'-dimethoxy)benzyl]pyrazolidine,
4-nitro-1,2-bis[(2',4'-dimethyl)benzyl]pyrazolidine,
4-nitro-1,2-di[(α-methylbenzyl)]pyrazolidine,
4-nitro-1,2-bis[(2',4'-dimethoxy)phenylethyl] pyrazolidine.

EXAMPLE 13

Following the procedure of Example 6, but substituting equal molar amounts of the following for 4-nitro-1,2-diethyl-pyrazolidine:
4-nitro-1,2-di[(3',4',5'-trimethoxy)benzyl]pyrazolidine,
4-nitro-1,2-bis[(3',4'-dimethoxy)benzyl]pyrazolidine,
4-nitro-1,2-bis[(2',4'-dimethyl)benzyl]pyrazolidine,
4-nitro-1,2-di(α-methylbenzyl)pyrazolidine,
4-nitro-1,2-bis[(2',4'-dimethoxy)phenylethyl] pyrazolidine,
there are obtained:
4-amino-1,2-di[(3',4',5'-trimethoxy)benzyl]pyrazolidine,
4-amino-1,2-bis[(3',4'-dimethoxy)benzyl]pyrazolidine,
4-amino-1,2-bis[(2',4'-dimethyl)benzyl]pyrazolidine,
4-amino-1,2-bis(α-methylbenzyl)pyrazolidine,
4-amino-1,2-bis[(2',4'-dimethoxy)phenylethyl] pyrazolidine.

What is claimed is:
1. A compound selected from those having the formula:

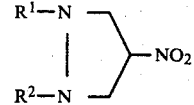

wherein; $R^1$ and $R^2$ are loweralkyl radicals containing from one to eight carbons, cyclic alkyl radicals containing from three to twelve carbons, or phehylloweralkyl wherein the loweralkyl group contains from one to eight carbons and the phenyl may be substituted with a nonreactive radical selected from the group consisting of lower alkyl, lower alkoxy, trifluoromethyl, halo, acetamido and sulfamoyl, and may be the same or different.

2. A compound of claim 1 which is 4-nitro-1,2-diethylpyrazolidine.

3. A compound of claim 1 which is 4-nitro-1,2-diisopropyl-pyrazolidine.

4. A compound of claim 1 which is 4-nitro-1,2-bis(4-methoxybenzyl)pyrazolidine.

5. A process for the preparation of 4-nitro-1,2-hydrocarbyl-pyrazolidine having the formula:

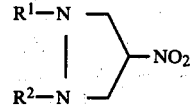

wherein; $R^1$ and $R^2$ are loweralkyl radicals containing from one to eight carbons, cyclic alkyl radicals containing from three to twelve carbons or phenylloweralkyl wherein the loweralkyl group contains from one to eight carbons and the phenyl may be substituted with a nonreactive radical selected from the group consisting of lower alkyl, lower alkoxy, trifluoromethyl, halo, acetamido and sulfamoyl, and may be the same or different, which comprises reacting a disubstituted hydrazine acid salt having the formula:

wherein $R^1$ and $R^2$ are as defined above and X is an acid anion, with a 1,3-bis(disubstituted amino)-2-nitropropane having the formula:

in the presence of a solvent therefor and at a temperature between room temperature and 150° C. to produce said 4-nitro-1,2-hydrocarbyl-pyrazolidine, wherein $R^3$, $R^4$, $R^5$ and $R^6$ are loweralkyl radicals containing from one to eight carbon atoms and may be the same or different and $R^3$ and $R^4$ or $R^5$ and $R^6$ taken together with the adjacent nitrogen atom may form a heterocyclic residue selected from the group consisting of pyrrolidino, morpholino, piperidino and piperazino.

6. A process of claim 5 wherein the 1,3-bis(disubstituted amino)-2-nitropropane is 1,3-dimorpholino-2-nitropropane.

7. A process of claim 5 wherein the disubstituted hydrazine acid salt is an acid salt of 1,2-diethyl hydrazine.

* * * * *